(12) United States Patent
Elibol et al.

(10) Patent No.: US 9,322,798 B2
(45) Date of Patent: Apr. 26, 2016

(54) DIAMOND ELECTRODE NANOGAP TRANSDUCERS

(75) Inventors: Oguz H. Elibol, Palo Alto, CA (US); Onur C. Akkaya, Stanford, CA (US); Grace M. Credo, San Mateo, CA (US); Jonathan S. Daniels, Palo Alto, CA (US); Noureddine Tayebi, Santa Clara, CA (US)

(73) Assignee: INTEL CORPORATION, Santa Clara, CA (US)

( * ) Notice: Subject to any disclaimer, the term of this patent is extended or adjusted under 35 U.S.C. 154(b) by 0 days.

(21) Appl. No.: 13/977,651

(22) PCT Filed: Dec. 15, 2011

(86) PCT No.: PCT/US2011/065154
§ 371 (c)(1),
(2), (4) Date: Jun. 28, 2013

(87) PCT Pub. No.: WO2013/089742
PCT Pub. Date: Jun. 20, 2013

(65) Prior Publication Data
US 2013/0281325 A1     Oct. 24, 2013

(51) Int. Cl.
*G01N 27/26* (2006.01)
*C12Q 1/68* (2006.01)
*C12Q 1/00* (2006.01)
(Continued)

(52) U.S. Cl.
CPC ............... *G01N 27/26* (2013.01); *C12Q 1/001* (2013.01); *C12Q 1/6874* (2013.01); *G01N 27/3278* (2013.01); *G01N 33/5438* (2013.01); *B82Y 15/00* (2013.01)

(58) Field of Classification Search
CPC ....... G01N 27/30; G01N 27/308; H01B 1/04; H01B 1/18; H01B 1/24
USPC ...................... 204/403.01–403.15, 409, 242; 205/777.5, 792; 422/82.01
See application file for complete search history.

(56) References Cited

U.S. PATENT DOCUMENTS

| 5,849,487 A | 12/1998 | Hase et al. |
| 5,866,323 A | 2/1999 | Markowitz et al. |

(Continued)

FOREIGN PATENT DOCUMENTS

| CN | 1957116 A | 5/2007 |
| WO | 2003/054225 A2 | 7/2003 |
| WO | 2013/089742 A1 | 6/2013 |

OTHER PUBLICATIONS

Panizza, et al. "Application of diamond electrodes to electrochemical processes", Electrochimica Acta, vol. 51, 2005, p. 191-199.*

(Continued)

*Primary Examiner* — J. Christopher Ball
(74) *Attorney, Agent, or Firm* — Pillsbury Winthrop Shaw Pittman LLP

(57) ABSTRACT

Embodiments of the invention provide transducers capable of transducing redox active chemical signals into electrical signals. Transducers comprise two electrodes separated by a nanogap. At least one electrode is comprised of conducting diamond. Methods of fabricating nanogap transducers and arrays of nanogap transducers are provided. Arrays of individually addressable nanogap transducers can be disposed on integrated circuit chips and operably coupled to the integrated circuit chip.

24 Claims, 8 Drawing Sheets

(51) Int. Cl.
   G01N 33/543    (2006.01)
   G01N 27/327    (2006.01)
   B82Y 15/00     (2011.01)

(56) References Cited

U.S. PATENT DOCUMENTS

| | | | |
|---|---|---|---|
| 6,232,075 | B1 | 5/2001 | Williams |
| 6,613,523 | B2 | 9/2003 | Fischer |
| 6,952,651 | B2 | 10/2005 | Su |
| 7,005,264 | B2 | 2/2006 | Su et al. |
| 7,211,390 | B2 | 5/2007 | Rothberg et al. |
| 7,488,578 | B2 | 2/2009 | Gumbrecht et al. |
| 7,575,865 | B2 | 8/2009 | Leamon et al. |
| 7,879,764 | B2 | 2/2011 | Su et al. |
| 7,923,240 | B2 | 4/2011 | Su |
| 8,262,900 | B2 | 9/2012 | Rothberg et al. |
| 8,372,585 | B2 | 2/2013 | Su et al. |
| 8,409,877 | B2 | 4/2013 | Liu et al. |
| 8,420,043 | B2 | 4/2013 | Gamo et al. |
| 8,500,979 | B2 | 8/2013 | Elibol et al. |
| 8,524,057 | B2 | 9/2013 | Rothberg et al. |
| 8,563,240 | B2 | 10/2013 | Su et al. |
| 8,574,892 | B2 | 11/2013 | Su |
| 2003/0113737 | A1 | 6/2003 | Pedersen |
| 2003/0152985 | A1 | 8/2003 | Pourmand et al. |
| 2003/0155942 | A1 | 8/2003 | Thewes |
| 2003/0215842 | A1 | 11/2003 | Sledziewski et al. |
| 2004/0005572 | A1 | 1/2004 | Rosner et al. |
| 2005/0019784 | A1 | 1/2005 | Su et al. |
| 2005/0026163 | A1 | 2/2005 | Sundararajan et al. |
| 2005/0106587 | A1 | 5/2005 | Klapproth et al. |
| 2005/0214759 | A1 | 9/2005 | Wlassof et al. |
| 2006/0014155 | A1 | 1/2006 | Hamers et al. |
| 2006/0199193 | A1 | 9/2006 | Koo et al. |
| 2008/0257720 | A1 | 10/2008 | Gobet et al. |
| 2009/0170716 | A1 | 7/2009 | Su et al. |
| 2010/0167938 | A1 | 7/2010 | Su et al. |
| 2010/0330553 | A1 | 12/2010 | Su et al. |
| 2011/0155586 | A1 | 6/2011 | Elibol et al. |
| 2011/0159481 | A1 | 6/2011 | Liu et al. |
| 2011/0319276 | A1 | 12/2011 | Liu et al. |
| 2012/0046176 | A1 | 2/2012 | Credo et al. |

OTHER PUBLICATIONS

Show, et al. "Characterization and electrochemical responsiveness of boron-doped nanocrystalline diamond thin-film electrode", Chemical Materials, vol. 15, No. 4, 2003, p. 879-888.*
E. Katelhon, et al. "Nanocavity redox cycling sensors for the detection of dopamine fluctuations in microfluidic gradients" Analytical Chemistry, vol. 82, No. 20, Oct. 2010, p. 8502-8509.*
International Search Report and Written Opinion received for PCT Patent Application No. PCT/US2011/065154, mailed on Sep. 24, 2012, 9 pages.
Fritz et al., "Electronic detection of DNA by its intrinsic molecular charge," PNAS, Oct. 29, 2002, pp. 14142-14146, vol. 99, No. 22.
Katelhon et al., "Nanocavity Redox Cycling Sensors for the Detection of Dopamine Fluctuations in Micro Gradients," Anal. Chem., 2010, pp. 8502-8509, vol. 82.
Zevenbergen et al., "Mesoscopic Concentration Fluctuations in a Fluidic Nanocavity Detected by Redox Cycling," Nano Letters, 2007, pp. 384-388, vol. 7, No. 2.
Delucia et al., "An error-prone family Y DNA polymerase (Din B homolog from Sulfolobus solfataricus) uses a 'stericgate' residue for discrimination against ribonucleotides," Nucleic Acids Research, 2003, pp. 4129-4137, vol. 31, No. 14.
Gao et al., "Conferring RNA polymerase Activity to a DNA polymerase: A single residue in reverse transcriptase controls substrate selection," Proc. Natl. Acad. Sci. USA, Biochemistry, 1997, pp. 407-411, vol. 94.
Wolfrum et al., "Nanofluidic Redox Cycling Amplification for the Selective Detection of Catechol," Analytical Chemistry, 2008, pp. 972-977, vol. 80, No. 4.

Elibol et al., "Localized heating and thermal characterization of high electrical resistivity silicon-on-insulator sensors using nematic liquid crystals," Applied Physics Letters, 2008, pp. 131908-1 to 131908-3, vol. 93, Issue 13, 131908.
Rolka et al., "Integration of a Capacitive EIS Sensor into a FIA System for pH and Penicillin Determination," Sensors, 2004, pp. 84-94, vol. 4, No. 6.
Elibol et al., "Nanoscale thickness double-gated field effect silicon sensors for sensitive pH detection in fluid," Applied Physics Letters, 2008, pp. 193904-1 to 193904-3, vol. 92, No. 19.
Goluch et al., "Redox cycling in nanofluidic channels using interdigitated electrodes," Analytical and Bioanalytical Chemistry, 2009, pp. 447-456, vol. 394, No. 2.
Gabig-Ciminska et al., "Electric chips for rapid detection and quantification of nucleic acids," Biosensors and Bioelectronics, 2004, pp. 537-546, vol. 19.
Kling, "Ultrafast DNA sequencing," Nature Biotechnology, 2003, pp. 1425-1427, vol. 21, No. 12.
Ronaghi et al., "DNA Sequencing: A Sequencing Method Based on Real-Time Pyrophosphate," Science Magazine, 1998, pp. 363-365, vol. 281, No. 5375.
Yeung et al., "Electrochemical Real-Time Polymerase Chain Reaction," Journal of American Chemical Society, 2006, 4 pages, vol. 128, No. 41.
Fuller et al., "The challenges of sequencing by synthesis," Nature Biotechnology, 2009, pp. 1013-1023, vol. 27, No. 11.
Eid et al., "Real-time DNA Sequencing from Single Polymerase Molecules," Science, 2009, pp. 133-138, vol. 323.
Rothberg et al., "An integrated semiconductor device enabling non-optical genome sequencing," Nature, 2011, pp. 348-352, vol. 475, No. 7356.
Wanunu et al., "Rapid electronic detection of probe-specific microRNAs using thin nanopore sensors," Nature Nanotechnology, 2010, pp. 807-814, vol. 5.
Ivanov et al., "DNA Tunneling Detector Embedded in a Nanopore," Nano Letters, 2010, pp. 279-285, vol. 11.
Margulies et al., "Genome sequencing in microfabricated high-density picoliter reactors," Nature, 2005, pp. 376-380, vol. 437.
Das et al., "Electrochemical Immunosensor Using p-Aminophenol Redox Cycling by Hydrazine Combined with a Low Background Current," Analytical Chemistry, 2007, pp. 2790-2796, vol. 79, No. 7.
Goldsmith et al., "Redox cycling and kinetic analysis of single molecules of solution-phase nitrite reductase," Proceedings of the National Academy of Sciences, 2011, pp. 17269-17274, vol. 108, No. 42.
Sun et al., "Electrochemistry of individual molecules in zeptoliter volumes," Journal of the American Chemical Society, 2008, pp. 8241-8250, vol. 130, No. 26.
Zevenbergen et al., "Stochastic Sensing of Single Molecules in a Nanofluidic Electrochemical Device," Nano Letters, 2011, pp. 2881-2886, vol. 11, No. 7.
Zevenbergen et al., "Fast Electron-Transfer Kinetics Probed in Nanofluidic Channels," Journal of the American Chemical Society, 2009, pp. 11471-11477, vol. 131, No. 32.
Elibol et al., "Nanoscale Thickness Double-gated Field Effect Silicon Sensors for Sensitive pH Detection in Fluid," Applied Physics Letters, 2008, pp. 193904 1-4, vol. 92.
Daniels et al., "Device and Method for Detecting Redox Reactions in Solution," U.S. Appl. No. 13/839,564, filed Mar. 13, 2013.
Weng et al., "Label-Free DNA Sensor by Boron-Doped Diamond Electrode Using an AC Impedimetric Approach," Anal. Chem., 2008, pp. 7075, vol. 80.
Compton et al.,"Electroanalysis at Diamond-Like and Doped-Diamond Electrodes," Electroanalysis, 2003, pp. 1349-1363, vol. 15, No. 17.
Granger et al.,"Standard Electrochemical Behavior of High-Quality, Boron-Doped Polycrystalline Diamond Thin-Film Electrodes," Anal.Chem., 2000, pp. 3793, vol. 72.
International Preliminary Report on Patentability received for PCT Patent Application No. PCT/US2011/065154, mailed on Jun. 26, 2014, 6 pages.
Japanese Office Action mailed May 19, 2015 for corresponding Japanese Patent Application No. 2014-544718 (5 pages).
Chinese Office Action mailed Oct. 23, 2015 for corresponding Chinese Patent Application No. 201180075483.6 (29 pages).

* cited by examiner

DIAMOND ELECTRODE NANOGAP TRANSDUCERS

CROSS-REFERENCE TO RELATED APPLICATIONS

This present application is the U.S. National Stage of PCT/US2011/065154, filed Dec. 15, 2011, the contents of which are hereby incorporated by reference herein in its entirety.

The present application is related to U.S. application Ser. No. 12/655,578 entitled "Nanogap Chemical and Biochemical Sensors," filed Dec. 31, 2009, now pending, U.S. patent application Ser. No. 11/226,696, entitled "Sensor Arrays and Nucleic Acid Sequencing Applications," filed Sep. 13, 2005, now pending, which is a continuation-in-part application that claims the benefit of U.S. patent application Ser. No. 11/073,160, entitled "Sensor Arrays and Nucleic Acid Sequencing Applications," filed Mar. 4, 2005, and U.S. patent application Ser. No. 11/967,600, entitled "Electronic Sensing for Nucleic Acid Sequencing," filed Dec. 31, 2007 now pending, the disclosures of which are incorporated herein by reference.

FIELD OF THE INVENTION

The embodiments of the invention relate generally to transducers, nanogap transducers, electronic sensing, electrochemistry, redox cycling, and biomolecule detection.

BACKGROUND INFORMATION

Analytic devices that provide increased accuracy and/or robustness, decreased need for analysis sample, and/or high throughput are valuable analytical and biomedical tools. Additionally, molecular detection platforms that are miniaturized and manufacturable in high volumes provide access to affordable disease detection to many people in places and situations in which such access was not in the past possible. The availability of affordable molecular diagnostic devices reduces the cost of and improves the quality of healthcare available. Additionally, portable molecular detection devices have applications in security and hazard detection and remediation fields and offer the ability to immediately respond appropriately to a perceived security or accidental biological or chemical hazard.

Genetic information in living organisms is contained in the form of very long nucleic acid molecules such as deoxyribonucleic acid (DNA) and ribonucleic acid (RNA). Naturally occurring DNA and RNA molecules are typically composed of repeating chemical building blocks called nucleotides. The human genome, for example, contains approximately three billion nucleotides of DNA sequence and an estimated 20,000 to 25,000 genes.

Determination of the entire three billion nucleotide sequence of the human genome has provided a foundation for identifying the genetic basis of many diseases, such as cancer, cystic fibrosis, and sickle cell anemia. Sequencing the genomes or sections of the genome of individuals provides an opportunity to personalize medical treatments. The need for nucleic acid sequence information also exists in research, environmental protection, food safety, biodefense, and clinical applications, such as for example, pathogen detection, i.e., the detection of the presence or absence of pathogens and/or their genetic varients.

DETAILED DESCRIPTION OF THE INVENTION

The ability to detect biological reactions and molecules at ultra-low concentrations has applicability to, for example, molecular detection and analysis, molecular diagnostics, disease detection, substance identification, and DNA detection and sequencing. Embodiments of the invention provide electronic sensors that are capable of detecting biological reactions and molecules and that exhibit high sensitivity, extremely reduced footprints, and a high degree of manufacturability. Nanogap transducers according to embodiments of the invention can be in the form of large arrays of nanogap transducers. For example, arrays of nanogap transducers comprising 1000 to 10 million or one million to 10 billion transducers in which 50% or more, 75% or more, 85% or more, 90% or more, 95% or more, or 98% or more of the transducers are functioning sensors are provided.

Embodiments of the invention provide transducers capable of functioning as electronic sensors and redox cycling sensors. In general, redox cycling is an electrochemical method in which a molecule that can be reversibly oxidized and/or reduced (i.e., a redox active molecule) moves between at least two electrodes that are biased independently, one below a reduction potential and the other one above an oxidation potential for the redox active molecule being detected, shuttling electrons between the independently biased electrodes (i.e., the molecule is oxidized at a first electrode and then diffuses to a second electrode where it is reduced or vice versa, it is first reduced and then oxidized, depending on the molecule and the potentials at which the electrodes are biased). In redox cycling the same molecule can therefore contribute a plurality of electrons to the recorded current resulting in the net amplification of the signal.

Nanogap transducers according to embodiments of the invention can be reliably fabricated in a CMOS (complementary metal oxide semiconductor) compatible manner allowing dense integration of sensor units (and optionally driving electronics) onto a single platform, such as for example a chip or silicon wafer typically used in integrated circuit manufacturing applications. Because the nanogap transducers provided by embodiments of the invention are very small and very sensitive, they provide the ability to detect molecules and biomolecules at ultra-low concentrations in a massively parallel manner. An individual nanogap transducer can, for example, occupy as little as $0.5\ \mu m^2$ on an array or other chip surface. In other embodiments an individual nanogap transducer occupies between to as $0.5\ \mu m^2$ to $50\ \mu m^2$ or $0.5\ \mu m^2$ to $100\ \mu m^2$ of area on an array or other chip surface. The ability to detect molecules in a highly sensitive manner has applications in fields of diagnostics, proteomics, genomics, security and chemical and biological hazard detection.

Figure 1:
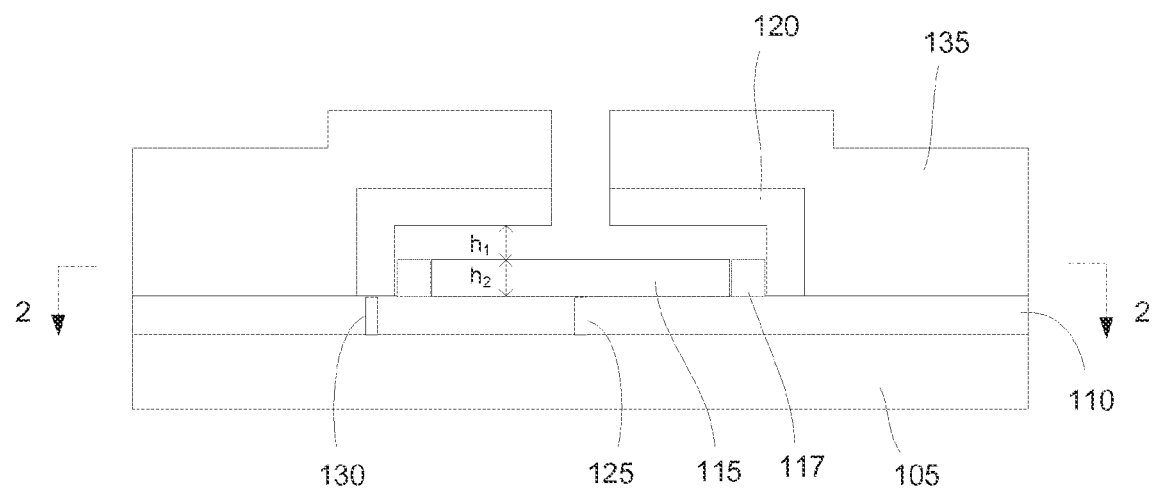
FIG. 1 is a schematic diagram illustrating a nanogap transducer.

FIG. 1 illustrates a nanogap transducer that is capable of functioning as an electronic sensor, detecting redox molecules, and/or functioning as a redox cycling sensor. In FIG.

1, a substrate 105 has a dielectric layer 110 and first electrode 115. A second electrode 120 is separated from the first electrode by a gap that has a height, $h_1$. In embodiments of the invention, the height of the gap, $h_1$, is less than 500 nm or between 10 and 200 nm, between 10 and 150 nm, or between 25 and 150 nm. Optional electronic interconnections 125 and 130, such as vias through dielectric layer 110, make connections to optional electronics (not shown) housed in the substrate 105. In embodiments of the invention, the substrate 105 is an integrated circuit (IC) chip and comprises electronics for, for example, driving electrodes 115 and 120, signal reading, signal amplification, and/or data output. The substrate can be other materials, such as, for example, glass, passivated metal, polymer, semiconductor, PDMS (polydimethylsiloxane), and/or flexible elastomeric substances. In embodiments in which the substrate does not house electronics, electrical connections to electrodes 115 and 120 can extend out along a surface of insulating layer 110 or through substrate 105, although other configurations are also possible. An insulating layer 135 is proximate to second electrode 120. The insulating layer 135 can be comprised, for example, of silicon dioxide, silicon nitride, silicon oxynitride, hafnium oxide, aluminum oxide, or, a polymer, such as polyimide. Other dielectric materials for insulating layer 135 are also possible.

The electrodes 115 and 120 are comprised of a conducting material, such as for example, diamond, platinum, and/or gold. In embodiments of the invention, at least one electrode 115 or 120 is comprised of a conducting diamond material. In embodiments of the invention, electrode 115 is comprised of conducting diamond. In further embodiments of the invention, both electrodes 115 and 120 are comprised of conducting diamond material. Diamond can be made to conduct electricity by doping it, for example. Dopants include, for example, boron, nitrogen, and phosphorous. In an embodiment of the invention, the dopant is boron. Doping concentrations for boron doped diamond materials include concentrations greater than $10^{20}$ atoms/cm$^3$ and less than $10^{22}$ atoms/cm$^3$. In embodiments of the invention, when the first electrode 115 is comprised of a conducting diamond material, the height of the electrode, $h_2$, is between 200 and 1000 nm. In alternate embodiments, the height of the conducting diamond electrode, $h_2$, is between 5 and 25 nm. In embodiments of the invention, the conducting diamond film is microcrystalline or nanocrystalline diamond. In further embodiments of the invention, optionally, a conducting diamond first electrode 115 has proximate dielectric regions 117. The dielectric material can be, for example, silicon dioxide, silicon nitride, silicon oxynitride, or other electrochemically non-reactive material that is compatible with a manufacturing process. In operation, typically a reference electrode (not shown) is also used with the nanogap transducer. The reference electrode is in contact with the solution which is being measured but does not have to be located within the nanogap.

Figure 2:
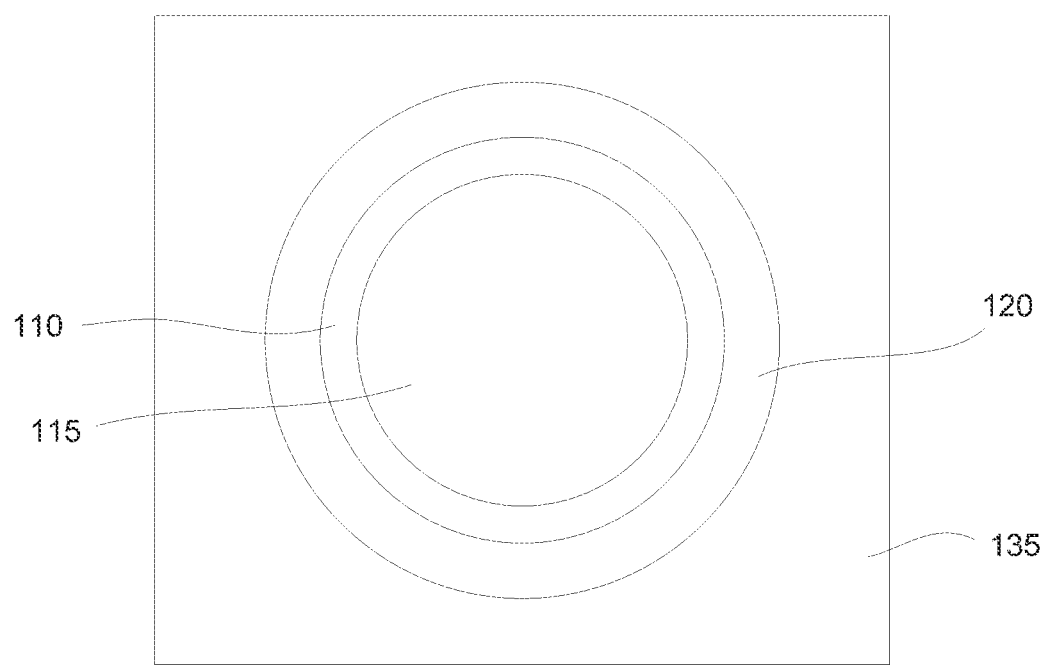
FIG. 2 is a schematic diagram illustrating a view along 2-2 of the nanogap transducer of FIG. 1.

FIG. 2, is a view along 2-2 of the nanogap transducer of FIG. 1. The features of FIG. 2 are the same as those described with respect to FIG. 1. Briefly, a first electrode 115, a dielectric layer 110, a second electrode 120, and an insulating layer 135 are depicted. Other shapes are possible for electrodes 115 and 120, such as, for example, oval, square, rectangular, triangular, or other multisided shape. Optional dielectric regions 117 are not shown in FIG. 2, but would be located in the region labeled 110.

Figure 3A:
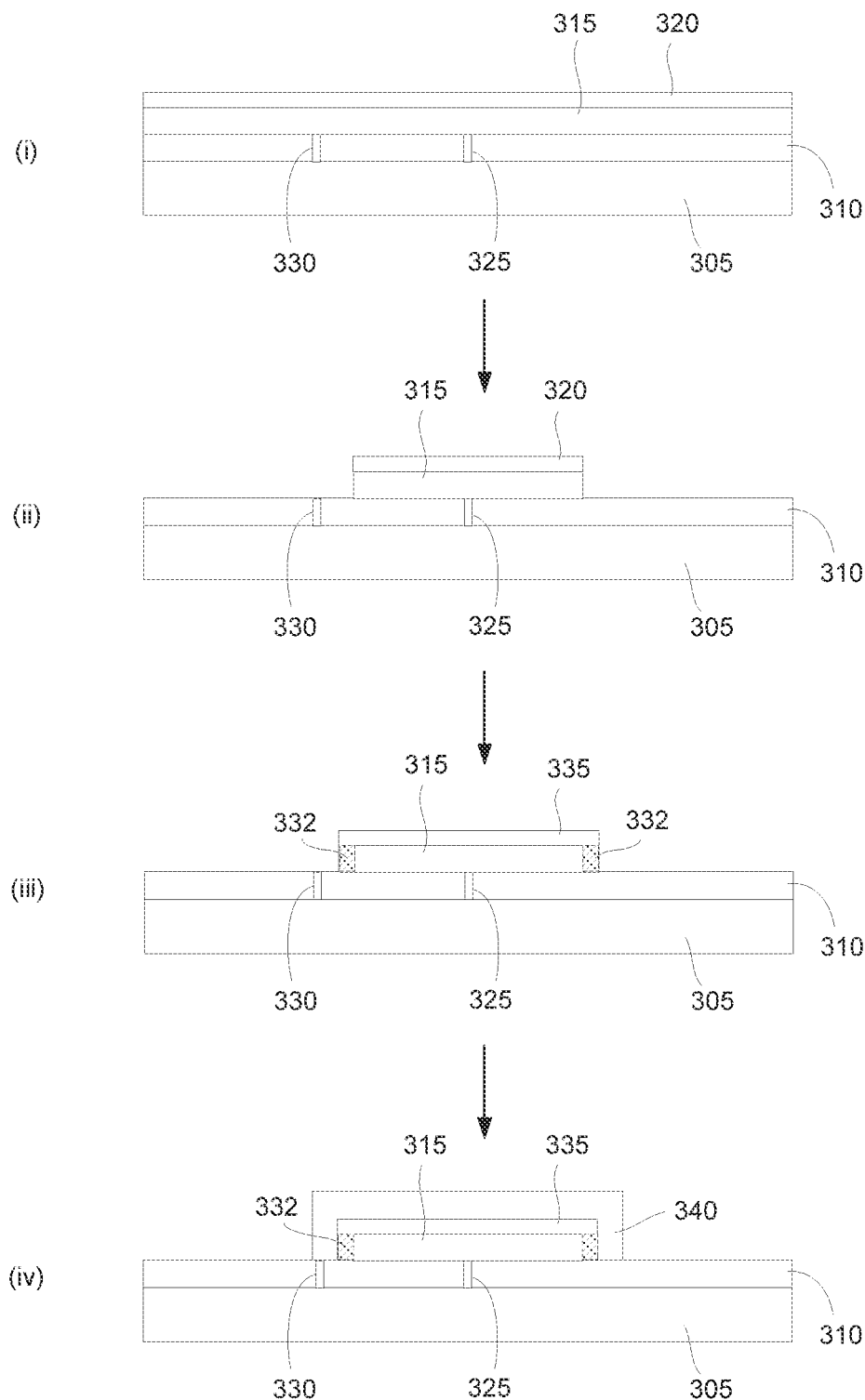
FIGS. 3A-B diagram a method for making a nanogap transducer having one or two electrodes comprised a conducting diamond material.
Figure 3B:
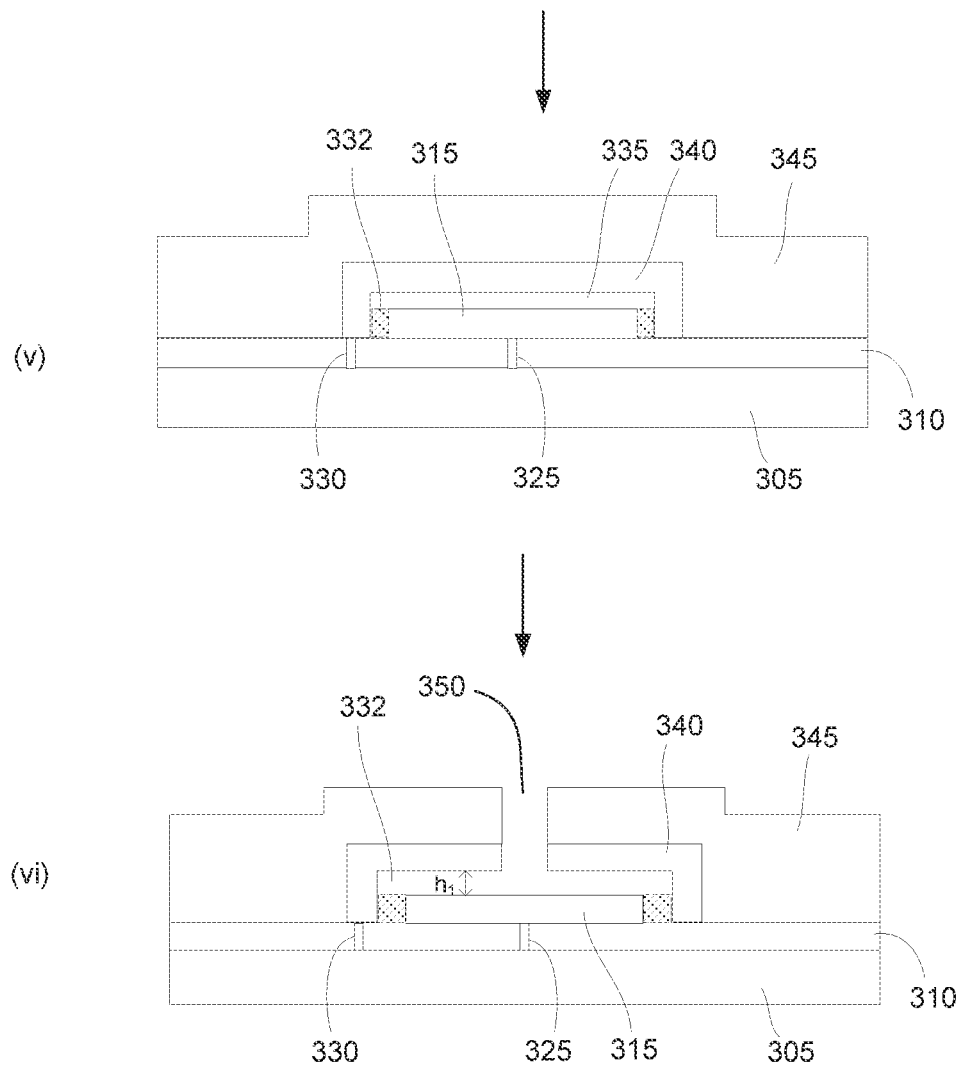

FIGS. 3A-B illustrate a method for making a nanogap transducer having a first electrode that is comprised of a conducting diamond material and optionally both a first and a second electrode that are comprised of a conducting diamond material. In FIG. 3A, structure (i) comprises a substrate 305, a dielectric layer 310, a first electrode layer 315 comprised of a conducting diamond material, and a hard mask layer 320. The conducting diamond material can be deposited, for example, using a hot filament CVD (chemical vapor deposition), a microwave plasma CVD, or a combustion flame assisted CVD process. The conducting diamond material can be deposited on a seed layer wherein the seed layer is deposited, for example by immersing the substrate in a solution that comprises diamond particles and attaching the particles to the surface using ultrasonication or by suspending diamond particles in a material that is spun onto the substrate surface. In embodiments of the invention, the conducting diamond material is boron doped diamond. In embodiments of the invention, the conducting diamond material is deposited with a boron doping concentration of greater than $10^{20}$ atoms/cm$^3$ and less than $10^{22}$ atoms/cm$^3$. In embodiments of the invention, the hard mask layer 320 is comprised of, for example, chromium or silicon dioxide. In embodiments of the invention, the substrate 305 is, for example, an IC chip comprising electronics for, for example, driving electrodes, signal detection, signal amplification, and/or data output. Optionally, conducting vias 325 and 330 are provided through the dielectric layer 310 to the substrate 305 that interconnect the electrodes with the optional electronics housed in the substrate 305. Other materials are also possible for substrate 305.

In embodiments of the invention, when the first electrode 315 is comprised of a conducting diamond material, it was found that it can be desirable to minimize the thickness of the first electrode in order to minimize the probability of shorting between the top and bottom electrodes. High aspect ratios for the first electrode were found to cause thinning of the sacrificial conformal coating at the edges of the electrode. However, it was also found that a minimum electrode height for the first electrode was necessary for microcrystalline diamond materials to avoid excessive surface roughness. It was found that excessive surface roughness of the first electrode could also cause openings in the sacrificial conformal coating and shorting between the first and the second electrodes. The height of the first electrode, when the first electrode is comprised of conducting diamond, in embodiments of the invention, can be between 300 and 1000 nm, between 300 and 800 nm, between 350 and 700 nm in order to balance height minimization with surface roughness considerations.

Structure (ii) of FIG. 3A can be created by patterning the hard mask layer 320, removing the hard mask layer 320 in unwanted regions, and etching the exposed diamond electrode layer 315. The exposed diamond electrode layer 315 can be etched, for example, using an oxygen plasma. An elevated temperature, such as between 70 and 100 C, can facilitate the oxygen plasma etch. The hard mask layer 320 is then removed and optionally the first electrode 315 surface is planarized by depositing a dielectric layer, such as, for example, silicon dioxide or silicon nitride, and performing a chemical mechanical polish (CMP) on the first electrode surface 315. The optional CMP process planarizes the electrode 315 surface and can improve the conformal coating properties of the following layers.

A conformal film of a sacrificial material 335 is deposited and patterned creating structure (iii) of FIG. 3A. The conformal film of sacrificial material 335 can be patterned by first depositing a photoresist, patterning the photoresist, depositing the sacrificial material, for example, by sputtering or atomic layer deposition (ALD), and lifting off the photoresist to define the conformal film of sacrificial material in the desired regions (a liftoff process). In embodiments of the invention, the sacrificial material comprises chromium or tungsten. The conformal film of sacrificial material 335 can be deposited, for example, by sputtering ALD deposition to achieve a film that wraps around the bottom electrode 315. In embodiments of the invention, the thin film of sacrificial material 335 has a thickness of less than 500 nm or between 10 and 200 nm, between 10 and 150 nm, or between 25 and 150 nm. In embodiments of the invention in which a dielectric layer is deposited and CMP is performed, optional dielectric regions 332 remain in the structure. In embodiments in which a dielectric layer is not deposited, regions 332 in structure (iii) of FIG. 3A comprise the conformal film of sacrificial material 335.

A second electrode material 340 is deposited on the conformal layer of sacrificial material 335 and patterned creating structure (iv) of FIG. 3A. The second electrode material 340 can be patterned lithographically using a liftoff process. In embodiments of the invention, the second electrode material is conducting diamond. Conducting diamond can be deposited, for example, by seeding and then depositing the layer using a hot filament CVD, a microwave plasma CVD, or a combustion flame assisted CVD process. In embodiments of the invention, when the second electrode 340 material is diamond, the conformal film of sacrificial material 335 comprises tungsten. In further embodiments of the invention, the second electrode 340 is comprised of platinum or gold. The platinum electrode can be deposited, for example, by sputtering a thin layer of chromium (which can be about 10 nm thick) as an adhesion layer and then sputtering a layer of platinum. The gold electrode material can be deposited, for example, by sputtering, evaporation, electrodeposition, or electroless deposition processes. In embodiments of the invention, the sacrificial material 335 is tungsten when the second electrode 340 is comprised of gold.

A dielectric layer 345 is then deposited on the structure (iv) of FIG. 3A, yielding structure (v) of FIG. 3B. The dielectric material can be, for example, silicon dioxide, silicon nitride, silicon oxynitride, hafnium oxide, aluminum oxide, or a polymer, although other materials are also possible. An access hole 350 is created through the dielectric layer 345 and the second electrode 340. The access hole 350 is created by defining a hole lithographically using a photoresist mask and then using a dry etching process to make the hole. The sacrificial material 335 is removed creating the gap between the first and second electrodes 315 and 340. The sacrificial material 335 can be removed using a wet etch, for example, in the embodiments in which the sacrificial material 335 is tungsten or chromium. The resulting structure is shown in FIG. 3B (vi). In embodiments of the invention, the height of the gap, $h_1$, is less than 500 nm or between 10 and 200 nm, between 10 and 150 nm, or between 25 and 150 nm. In embodiments in which a CMP process was used to planarize the first electrode 315, regions 332 comprise a dielectric material, such as silicon dioxide, and in embodiments in which a dielectric deposition and CMP were not used, regions 332 are empty.

Dielectric materials also include, for example, silicon dioxide, silicon nitride, siliconoxynitride, carbon doped oxide (CDO), silicon carbide, organic polymers such as perfluorocyclobutane or polytetrafluoroethylene, fluorosilicate glass (FSG), and/or organosilicates such as silsesquioxane, siloxane, or organosilicate glass. Dielectric materials can also include polymers, such as, for example, polyimide.

Figure 4A:
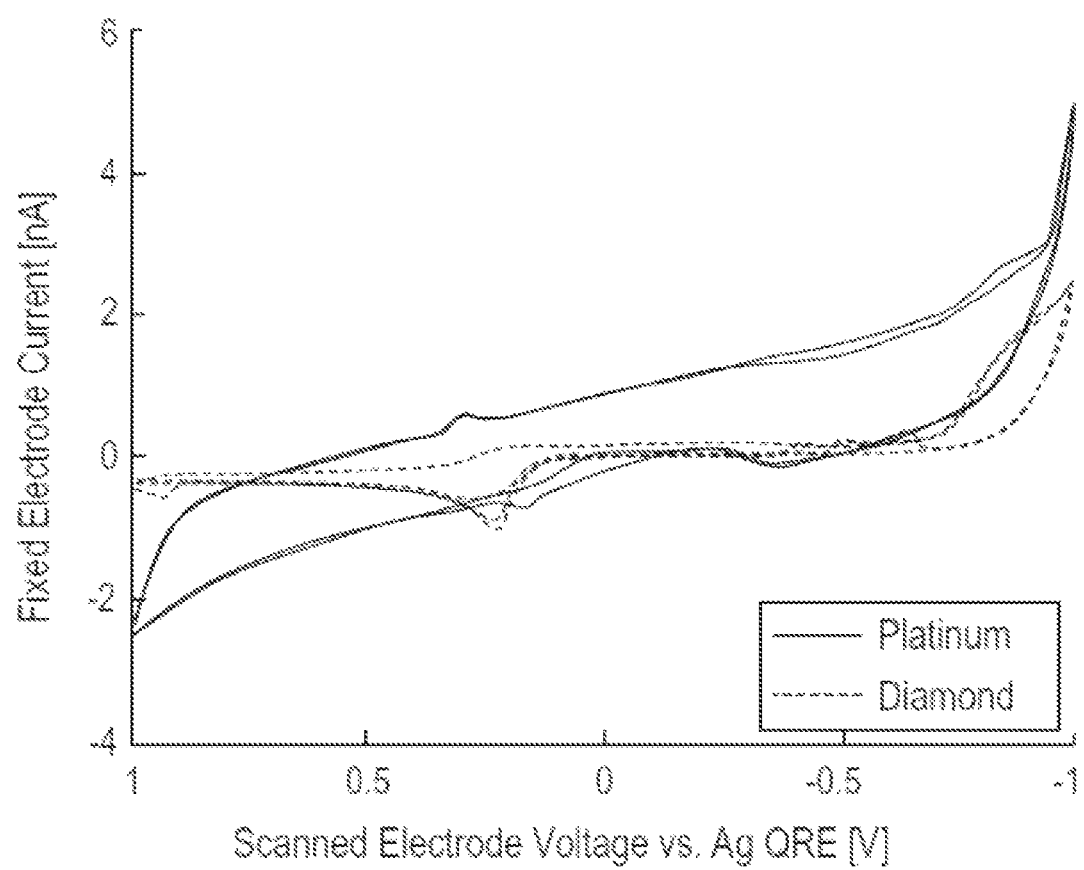
FIGS. 4A-B graph cyclic voltammetric measurements for a nanogap transducer having a conducting diamond electrode.
Figure 4B:
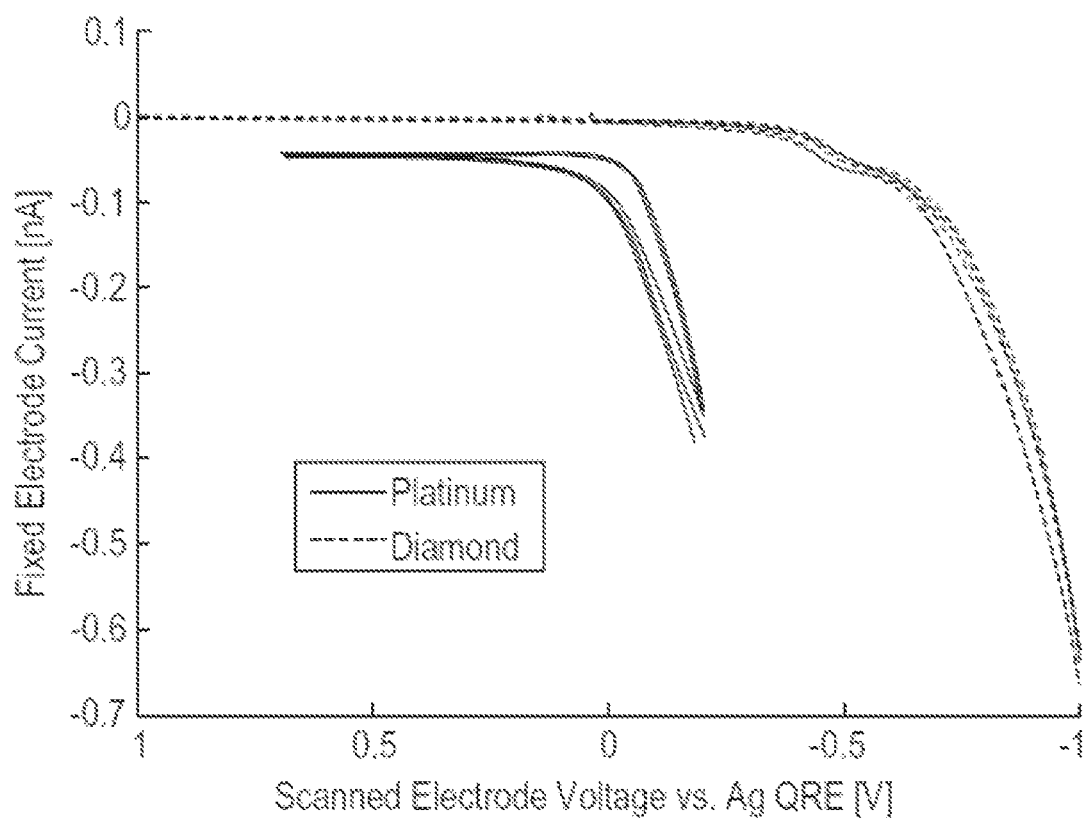

FIGS. 4A-B illustrate cyclic voltammetric graphs for a nanogap transducer having a conducting diamond first electrode and a platinum second electrode according to embodiments of the invention. It can be seen from FIGS. 4A-B that it is possible to make operational nanogap transducers having a diamond electrode that do not exhibit first-second electrode shorting. In FIG. 4A, the electrode current is plotted as a function of the electrode potential using a model compound (ferrocene) having a redox potential at about 0.240 V. Measurements were taken in phosphate buffered saline solution versus a silver wire reference electrode (Ag quasi-reference electrode (QRE).) Although a high background current is observed with the platinum electrode, advantageously it was found that the background current with the conducting diamond electrode was minimal. FIG. 4B illustrates cyclic voltammetry measurements using a buffer solution with the nanogap transducer. The larger operational voltage window of the diamond electrode and significantly reduced background current compared to platinum electrode (diamond electrode registering dose to no current while platinum electrode has an offset current due to background current) can be seen from FIG. 4B.

Because the background current with the conducting diamond electrode is small, it is possible to record measurements on small numbers of molecules using only one of the two working electrodes. Measurements can be recorded on as few as one molecule. In alternate embodiments, measurements recorded at both of the electrodes are used to generate the signal. A system for measuring and recording electrode potentials and current flow in nanogap transducers includes, for example, a bipotentiostat. Using a bipotentiostat, the potential of both electrodes versus the solution potential is controlled and the current flowing through the electrodes is measured. Some or all of the parts of a system for driving electrodes and measuring and recording current flow can be located in an integrated circuit (IC) chip that is electrically coupled to an array of individually addressable nanogap transducers housed on the IC chip. In embodiments of the invention, a computer system associated with the array of individually addressable nanogap transducers comprises software for measuring and recording electrode potential and current values using measurements from only one electrode where the electrode is comprised of conducting diamond. In alternate embodiments the computer system includes software for measuring and recording electrode potentials from two electrodes and/or both two electrodes and one electrode. Techniques such as electrochemical correlation spectroscopy can be used to produce a signal from measurements from two oppositely biased electrodes in a nanogap device.

In general, electronic sensors employing electrodes, such as nanogap transducers, are capable of measuring the impedance, the resistance, the capacitance, and/or the redox potential of the materials that are located on or near the electrode surface. The substrate on which the nanogap transducers reside may also include detection and/or drive circuits, logic for switching, latches, memory, and/or input/output devices. Optionally some or all of the electronics for sensing and driving electrodes and recording data are integrated circuits that are part of the substrate that houses an array of nanogap transducers. Electronics providing input and output control are optionally housed in the substrate, such as in an integrated circuit chip, or are provided through circuitry that is external the substrate. An array of nanogap transducers is optionally equipped with circuitry for individually addressing the electrodes, driving the electrodes at selected voltages, memory for storing voltage current information to be supplied to the electrodes, memory and microprocessors for measuring electrode characteristics, differential amplifiers, current-sensing circuits (including variants of circuits used in CMOS image sensors), and/or field effect transistors (direct and floating gate). Alternatively, one or more of these functions can be performed by external instruments and/or attached computer system(s).

In a redox cycling measurement, oppositely biased electrodes are used to repeatedly flip the charge state of redox active molecules in solution allowing each redox active molecule to participate in multiple redox reactions and thereby contribute multiple electrons to a measured current value. In redox cycling measurements, the height of the gap between the electrodes is on the nanometer scale. Redox active molecules in the cavity between the two electrodes shuttle multiple electrons between the electrodes, leading to amplification of the measured electrochemical current. Signals from the redox active species can potentially be amplified greater than 100 times, depending on factors such as the stability of the redox species and the ability of the redox species to diffuse out of the sensing region.

In embodiments of the invention, electrodes in the nanogap transducer are independently biased at the oxidation and reduction potential of the redox species to be detected. Redox species act as charge shuttles and the diffusion of the molecules from one electrode to the other results in the reduction and oxidation of the redox molecule and a net charge transfer. The magnitude of current through either electrode is proportional to the analyte (redox species) concentration in the cavity. The gaps between the electrodes are optionally sealed with beads to prevent the diffusion of the redox active species out of the cavity, thereby increasing the effective concentration of the redox species. Sealing of the cavity can prevent the escape of redox species from the cavity during sensor measurements.

In general, a redox active species is a molecule that is capable of reversibly cycling through states of oxidation and/or reduction a plurality of times.

In embodiments of the invention, nanogap transducers can be arrays of individually-addressable nanogap transducers. Arrays are built having a variety of dimensions and numbers of nanogap transducer. The selection of number layout of nanogap transducers is informed by factors such as, for example, the types and numbers of analytes to be detected, the size of the sensing regions, and costs involved in manufacturing the arrays. For example, arrays of nanogap transducers are 10×10, 100×100, 1,000×1,000, $10^5 \times 10^5$, and $10^6 \times 10^6$. Very high density, high density, moderate density, low density, or very low density arrays can be made. Some ranges for very high-density arrays are from about 100,000,000 to about 1,000,000,000 sensors per array. High-density arrays range from about 1,000,000 to about 100,000,000 sensors. Moderate density arrays range from about 10,000 to about 100,000 sensors. Low-density arrays are generally less than 10,000 cavities. Very low-density arrays are less than 1,000 sensors.

An array of individually addressable nanogap transducers can be housed on and electrically coupled to an IC chip. The IC chip is typically built on a semiconductor substrate, such as, a semiconductor wafer that is diced apart to yield individual IC chips. The base substrate on which an IC chip is built is typically a silicon wafer, although embodiments of the invention are not dependent on the type of substrate used. The substrate could also be comprised of germanium, indium antimonide, lead telluride, indium arsenide, indium phosphide, gallium arsenide, gallium antimonide, and/or other group III-V materials either alone or in combination with silicon or silicon dioxide or other insulating materials. Layers and layers comprising devices can also be described as the substrate or part of the substrate on which embodiments of the invention are housed or fabricated.

The nanogap transducer arrays allow, for example, a large number of immobilized DNA molecules to be sequenced simultaneously, although other uses are also possible. The immobilized DNA molecules can either be a sample to be sequenced or capture DNA probes of known sequence can be first immobilized and then the sample to be sequenced can be hybridized to the immobilized probes. The capture probes have a sequence designed to hybridize to sections of the sample DNA. In embodiments of the invention, DNA fragments (or capture probes) to be immobilized are diluted so that statistically each sensor has one DNA molecule immobilized. Sequence information is assembled from the nanogap transducers having a single DNA molecule immobilized. Information from nanogap transducers showing ambiguous results can be disregarded.

Figure 5:
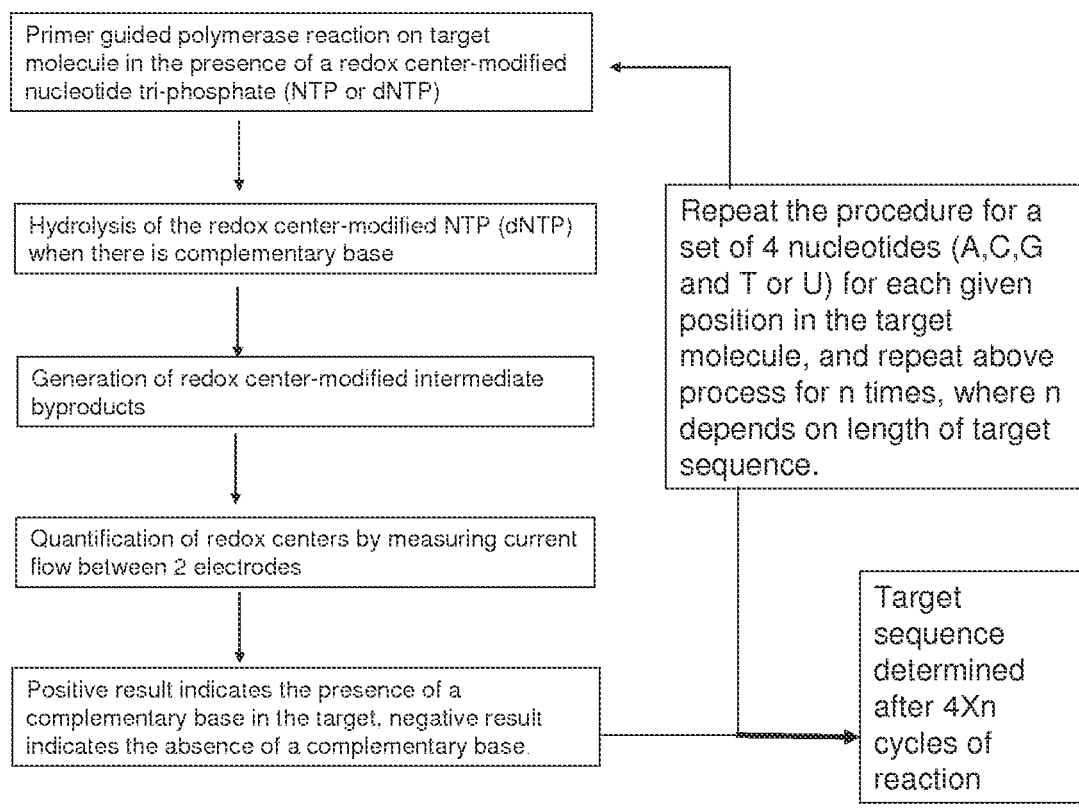
FIG. 5 provides a flow diagram of a method for determining the sequence of a nucleic acid molecule.

Methods are provided for sequencing nucleic acids in which amplification of the nucleic acid sample (i.e., increasing the number of copies of the nucleic acid molecules in the sample) optionally does not have to occur. FIG. 5 provides a flow diagram describing a method that is useful for sequencing a nucleic acid molecule, SNP (single nucleotide polymorphism) detection, and gene expression detection. In FIG. 5, a nucleic acid molecule is attached to a surface inside an electronic sensor. A solution is provided to the sensor cavity containing a primer complementary to a section of the nucleic acid target. The primer DNA molecule hybridizes to a section of the DNA molecule attached inside the cavity and primes the attached DNA molecule for synthesis of a complementary strand of DNA. If the sequence of DNA inside the cavity is unknown, the primer might be one of many having random sequences provided to the DNA strand inside the sensor. The primer can be terminated with a nuclease-resistant nucleotide. After the primer is allowed to hybridize to the DNA molecule inside the cavity, a solution containing a DNA polymerase enzyme and a redox-center modified nucleotide triphosphate (NTP or dNTP) is added. The dNTP contains either a reodox modified deoxyadenosine triphosphate (dATP), deoxycytidine triphosphate (dCTP), deoxyguanosine triphosphate (dGTP), deoxythymidine triphosphate (dTTP), or uridine triphosphate (UTP). For example, if a redox-modified dATP has been provided and thymidine is the next complementary nucleic acid in the sequence, then the redox-modified dATP is incorporated into the growing DNA strand. Where there is a cytosine on the strand to be sequenced, a guanine will be incorporated, where there is a thymidine, an adenosine will be incorporated, and vice versa. If dATP is not the next complementary nucleic acid, then no chemistry occurs inside the sensor cavity. Products of the reaction are then detected. If no reaction has occurred, then the redox-center modified reaction products are not detected. Thus, a positive result (the detection of redox-center modified reaction products) indicates that dATP (in this example) is the next complementary nucleic acid in the growing chain. If a negative result is found, this method is then repeated for the three remaining redox-center modified nucleotides until a positive result is achieved to determine the identity of the complementary base. After the identity of a nucleotide has been determined, the growing strand of complementary DNA can be terminated with a nuclease resistant nucleotide.

Figure 6:
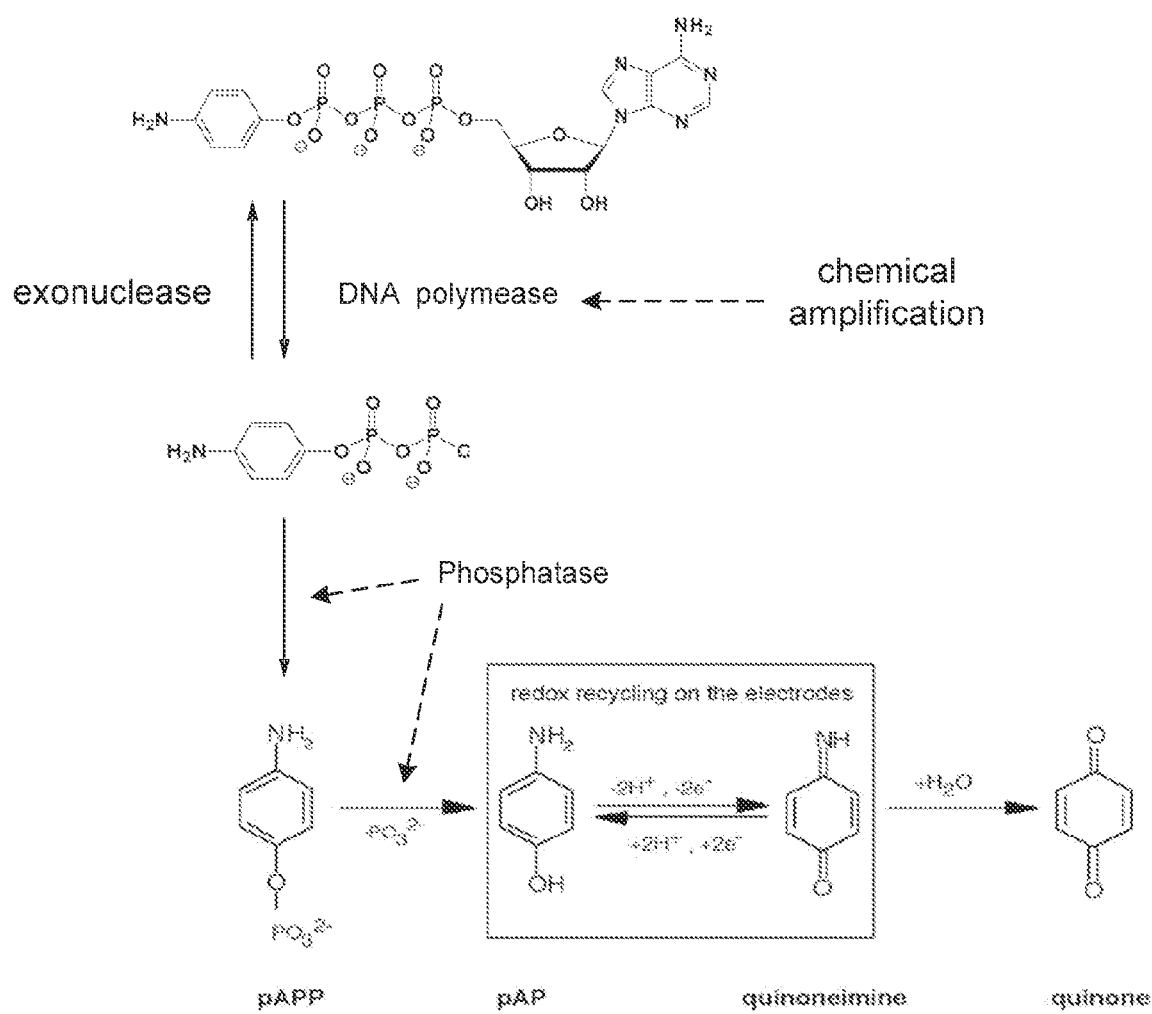
FIG. 6 provides a reaction scheme showing a method for sequencing a nucleic acid molecule through the detection of an oxidation-reduction reaction of a redox active species.

FIG. 6 illustrates a method for sequencing a DNA molecule through chemically amplifying the redox signal obtained when a nucleotide base is complementary to the base provided by the template strand being sequenced. The method of FIG. 6 provides for chemical amplification of the signal when a complementary base in incorporated into a growing complementary strand. The primed growing DNA molecule is terminated with a nuclease resistant base through the action of a polymerase enzyme. In this example, the redox labeled NTP is γ-aminophenyl-adenine-triphosphate (dATP). The incorporation of a complementary redox labeled nucleotide into the growing strand releases the redox labeled pyrophosphate (PPi) group into solution. The action of a phosphatase enzyme removes the pyrophosphate from the redox molecule. Useful phosphatase enzymes include, for example, alkaline phosphatase, acid phosphatase, protein phosphatase, polyphosphate phosphatase, sugar-phosphatase, and pyrophosphatase. In this example, the redox active species is the p-aminopheonol (pAP) and quinoneimine pair. The number of p-aminopheonol molecules released into solution is amplified through the cycling of the redox labeled NTP incorporation and excision reactions. Specifically, a complementary redox labeled nucleotide is incorporated, an exonuclease enzyme removes the incorporated complementary nucleotide, and then DNA polymerase incorporates a second redox labeled complementary nucleotide and a second redox labeled pyrophosphate group is released into solution. Through these repeated cycles of incorporation and removal, the concentration of the redox active species builds up in solution. In this way, the signal resulting from the incorporation of a complementary base into the growing complementary strand is amplified. The removal of the phosphate groups activates the redox active species. The presence of the redox active species free of phosphate groups is detected electrochemically. The redox active species can be recycled between two electrodes of a nanogap transducer to amplify the signal further via a redox cycling reaction. As described more fully herein, the signal amplification technique of cycling redox active species between electrodes is referred to as redox cycling. By moving between electrodes of a nanogap transducer, each redox active species contributes multiple electrons to the measured current, thereby amplifying the measured current. If the nucleotide supplied to the reaction is not complementary to the growing DNA strand, then the free redox active species is not detected. Once a nucleotide incorporation has been detected, the growing strand is provided with a nuclease-resistant base that is complementary to the next space in the template DNA molecule that is being sequenced.

A redoxigenic nucleotide has a redox active species attached to the γ-phosphate group of the nucleoside. The base for the redoxigenic nucleotide may be an A, G, C, or T. Redox active species include, for example, aminophenyl, hydroxyphenyl, and/or napthyl groups. A redox active species may also be attached to the nucleotide base. The base may be an A, G, C, or T and the redox active species may be, for example a ferrocene, an anthraquinone, or a methylene blue molecule. A third redox active group attachment motif includes one in which the redox active group is attached to the sugar group of the nucleotide base. For the sugar-attached redox-modified nucleotide, the base may be an A, G, C, or T and the redox active species may be, for example a ferrocene, an anthraquinone, or a methylene blue molecule.

Polymerases are available that can incorporate ribonucleotides or modified nucleotides into DNA, such as for example, the commercially available Therminator DNA polymerase (available from New England Biolabs, Inc., Beverly, Mass.) or genetically engineered DNA polymerase. See also, for example, DeLucia, A. M., Grindley, N. D. R, Joyce, C. M., *Nucleic Acids Research,* 31:14, 4:129-4137 (2003); and Gao, G., Orlova, M., Georgiadis, M. M., Hendrickson, W. A., Goff, S. P., *Proceedings of the National Academy of Sciences,* 94, 407-411 (1997). Nuclease-resistant nucleotides can be ribonucleotides or other modified nucleotides. Exemplary nuclease resistant bases that can be incorporated into growing DNA strands hut that are resistant to digestion by exonucleases (such as the 3' to 5' exonuclease active DNA polymerases or exonuclease I and III) include alpha phosphorothioate nucleotides (available from Trilink Biotechnologies, Inc., San Diego, Calif.). Additionally, ribonucleotides can be incorporated into a growing DNA strand by Therminator DNA polymerase or other genetically engineered or mutated polymerases, but the ribonucleotide bases are resistant to digestion by exonucleases, such as exonucleases I or exonuclease III (available from New England Biolabs). Exemplary nucleases that cannot digest these resistant bases include exonuclease I, nuclease III, and 3' to 5' exonuclease active DNA polymerases.

In embodiments of the invention, a single nucleic acid molecule to be sequenced is attached to a surface inside a nanogap transducer. The nucleic acid is primed with a complementary strand that is terminated with a nuclease resistant nucleotide. A complementary redox-modified dNTP molecule is incorporated into the growing strand through the action of a DNA polymerase enzyme present in the solution in the nanogap transducer cavity. The electrodes of the nanogap transducer are oppositely biased at the redox potential of the redox species, and when the redox species is present, a current flow is detected at the electrode surfaces. The excess redox-modified dNTP from the polymerase reaction is washed away from the reaction site Any incorporated dNMP is then excised from the growing complementary DNA strand through the action of a nuclease enzyme present in the solution in the electrode cavity. This method is then optionally repeated for the three other nucleotides. Once the next complementary nucleotide has been determined, the growing complementary nucleic acid strand can be terminated with a complementary nuclease resistant base and the next complementary base can be determined.

In alternate embodiments, more than one copy of the nucleic acid molecule to be sequenced is attached in the electrode cavity. The attachment of a plurality of copies of the nucleic acid to be sequenced amplifies the signal detected when a complementary nucleotide triphosphate is provided to the cavity. The detected signal can then optionally be amplified further through redox cycling techniques.

Nucleic acid sequencing can be performed in a massively parallel manner using arrays of individually addressable nanogap transducers. A sample comprising nucleic acid molecules is presented to the array in a manner that results in statistically one nucleic acid molecule per reaction cavity. Electronics coupled to the reaction cavities detect the incorporation of nucleic acids in the cavities. Data from cavities that is inconsistent can be discarded. Sequence information for each nucleic acid in a cavity is built through multiple reaction cycles.

One or more surfaces of the nanogap transducer can be optionally functionalized with, for example, one of or combination of amine, aldehye, epxoy, thiol, groups, and molecules to be attached are functionalized with amine (for surface bearing carboxy, epoxy, and/or aldehyde functional groups) and carboxyl for surface bearing amine groups), thiol (for surface of gold) to facilitate molecular attachment. Various conjugation chemistries are available to join the functional groups (for example, EDC for amine-carboxyl). The concentration of molecules on the substrate surface is controlled, for example, in several ways: by limiting the density of surface functional groups or by limiting the quantity of molecules to be attached. DNA is immobilized on a surface, for example, by using acrydite-modified DNA fragments that are attached to a surface modified with thiol groups. Amine-modified DNA fragments can be attached to epoxy or aldehyde modified surfaces.

A sensor system including one or more arrays of nanogap transducers (such as an array of nanogap transducers on a IC device surface), electronics for driving the transducers and recording measurements, and a computer for recording an analyzing data, can also include fluid delivery systems that are capable of delivering fluids to the nanogap transducers. The fluidic system can comprise reservoirs for reagents, pumps and mixing chambers, washing solutions, waste chambers, and fluid delivery systems that deliver fluids to the surface of an array of nanogap transducers.

In general, the types of nucleic acids that can be sequenced include polymers of deoxyribonucleotides (DNA) or ribonucleotides (RNA) and analogs thereof that are linked together by a phosphodiester bond. A polynucleotide can be a segment of a genome, a gene or a portion thereof, a cDNA, or a synthetic polydeoxyribonucleic acid sequence. A polynucleotide, including an oligonucleotide (for example, a probe or a primer) can contain nucleoside or nucleotide analogs, or a backbone bond other than a phosphodiester bond. In general, the nucleotides comprising a polynucleotide are naturally occurring deoxyribonucleotides, such as adenine, cytosine, guanine or thymine linked to 2'-deoxyribose, or ribonucleotides such as adenine, cytosine., guanine, or uracil linked to ribose. However, a polynucleotide or oligonucleotide also can contain nucleotide analogs, including non-naturally occurring synthetic nucleotides or modified naturally occurring nucleotides.

Data from the sensors can be analyzed as follows. If a nanogap transducer has more than one DNA molecule attached within its cavity, there will be more than one possible reading from at least one of the sequenced positions. Therefore, only data from those nanogap transducers having one molecule attached in the nanogap transducer cavity (an effective sensor) are used in the sequence analysis. Sequences of effective sensors are aligned by computer program. The sequence information can be used as de novo sequencing information or reference sequencing information. Further analysis is performed depending on the quality of the data and purpose of the sequencing task.

Additionally, nanogap transducers according to embodiments of the invention are capable of performing a variety of biologically important detections which are not limited to those described herein. For example, nanogap transducers are capable of detecting mutations in DNA and identifying pathogens through DNA sequencing reactions. Additionally, electronic sensors are used to diagnose diseases through assaying metabolic enzyme activities. Pyrophosphate is a byproduct of many enzymatic reactions that are part of metabolic and signal transduction pathways. Nanogap transducers according to embodiments can be provided with recognition and binding sites for a target analyte. The nanogap transducer is created having the recognition and binding site of interest and a test is performed on a sample solution by exposing the sample solution to the analyte binding region of the biosensor device to allow binding of any specifically recognized biomolecules of interest. The nanogap transducer(s) can be integrated into micro- or nanofluidic systems that provides filtering and sample purification functions. Thus, an enzyme to be tested for functionality is bound in the electronic biosensor and a reaction solution is provided in which a reaction product is PPi labeled with a redox center. For example, a biosensor device probes the functionality of adenylating enzymes that convert fatty acids to acyl adenylate and produce PPi by binding the adenylating enzyme of interest in the biosensor device and providing fatty acid substrates as well as ATP in a reaction solution. Additional examples include catechols. In further examples, living microbes are specifically bound to biosensors. Microbes are optionally bound in the sensing device through an antibody that specifically recognizes a surface antigen on the microbe. Antibody sandwich assays are performed. In the antibody sandwich assay, an electronic sensor is provided having an antibody specific for the molecule to be detected, the sensor is exposed to the molecule to be detected, and a second antibody specific for a different epitope of the molecule to be detected is bound to the molecule to be detected. The second antibody has an attached molecule capable of converting redox labeled ATP to redox labeled PPi. The redox labeled PPi is detected through redox cycling. Redox labels include, for example, ferrocene, anthraquinone, and methylene blue molecules, and aminophenyl, hydroxyphenyl, and/or napthyl groups.

A computer or computer system comprises a processing system, including one or more processors that are communicatively coupled to one or more volatile or non-volatile data storage devices, such as random access memory (RAM), read-only memory (ROM), mass storage devices such as serial advanced technology attachment (SATA) or small computer system interface (SCSI) hard drives, and/or devices capable of accessing media, such as floppy disks, optical storage, tapes, flash Memory, memory sticks, CD-ROMs and/or digital video disks (DVDs). The term ROM refers to non-volatile memory devices such as erasable programmable ROM (EPROM), electrically erasable programmable ROM (EEPROM), flash ROM, and/or flash memory. The processor can also be communicatively coupled to additional components, such as graphics controllers, memory interface hubs, SCSI (small computer system interface) controllers, network controllers, network interfaces, and universal serial bus (USB) controllers. Some or all of the communications between elements of the computer system, additional processors, and/or external computers and computer networks can also occur using various wired and/or wireless short range protocols including, USB, WLAN (wireless local area network), radio frequency (RE), satellite, microwave, Institute of Electrical and Electronics Engineers (IEEE) 802.11, Bluetooth, optical, fiber optical, infrared, cables, and lasers. Typically a computer system is also coupled to other input/output devices, such as, for example, display screens, keyboards, trackpads, mice.

Persons skilled in the relevant art appreciate that modifications and variations are possible throughout the disclosure as are substitutions for various components shown and described. Reference throughout this specification to "one embodiment" or "an embodiment" means that a particular, feature, structure, material, or characteristic described in connection with the embodiment is included in at least one embodiment of the invention, but does not necessarily denote that they are present in every embodiment. Furthermore, the particular features, structures, materials, or characteristics disclosed in the embodiments may be combined in any suitable manner in one or more embodiments. Various additional layers and/or structures may be included and/or described features may be omitted in other embodiments.

We claim:

1. A device comprising, a substrate having a surface, and a transducer disposed on the substrate surface, wherein the transducer comprises:

a first electrode and a second electrode, wherein the first or the second electrode is comprised of conducting diamond, wherein the first and the second electrodes are each coupled to conducting lines through which voltage can be applied to the first and second electrodes independently and a current measured from each of the first and second electrodes independently, and wherein the first electrode has a face and the second electrode has a face and the face of the first electrode is separated from the face of the second electrode by a distance that is between 10 and 200 nm, a cavity capable of containing a fluid between the face of the first electrode and the face of the second electrode, and an access hole through the second electrode that is capable of allowing a fluid to enter and leave the cavity, wherein the substrate is an integrated circuit chip.

2. A device comprising, a substrate having a surface, and a transducer disposed on the substrate surface, wherein the transducer comprises:
a first electrode and a second electrode, wherein the first or the second electrode is comprised of conducting diamond, wherein the first and the second electrodes are each coupled to conducting lines through which voltage can be applied to the first and second electrodes independently and a current measured from each of the first and second electrodes independently, and wherein the first electrode has a face and the second electrode has a face and the face of the first electrode is separated from the face of the second electrode by a distance that is less than 500 nm, a cavity capable of containing a fluid between the face of the first electrode and the face of the second electrode, and an access hole through the second electrode that is capable of allowing a fluid to enter and leave the cavity, wherein the substrate is an integrated circuit chip and the first electrode and the second electrode are independently electrically coupled to electronics within the integrated circuit chip through the conducting lines.

3. The device of claim 2 wherein the conducting diamond is nanocrystalline diamond.

4. The device of claim 2 wherein the conducting diamond is boron doped diamond.

5. The device of claim 2 wherein both the first and second electrodes are comprised of conducting diamond.

6. The device of claim 2 wherein the first electrode is comprised of conducting diamond and the height of the first electrode is between 300 nm and 1000 nm.

7. The device of claim 2 wherein the first or the second electrode is comprise of gold or platinum.

8. The device of claim 1, wherein the second electrode surrounds at least the face the first electrode and both sides of the first electrode.

9. The device of claim 2 wherein the face of the first electrode is separated from the face of the second electrode by a distance that is between 10 and 200 nm.

10. A device comprising, an integrated circuit chip having a surface, and an array of transducers disposed on the integrated circuit chip surface, wherein the array comprises at least 1000 transducers and at least 85% of the transducers are functional transducers, wherein transducers that make up the array are electrically coupled to and individually addressable through electronics in the integrated circuit chip, and wherein a transducer comprises: a first electrode and a second electrode, wherein the first or the second electrode is comprised of conducting diamond, wherein the first and second electrodes are independently coupled to the integrated circuit chip through which voltage can be applied to the first and second electrodes and a current measured from each of the first and second electrodes independently, and wherein the first electrode has a face and the second electrode has a face and the face of the first electrode is separated from the face of the second electrode by a distance that is less than 500 nm, a cavity capable of containing a fluid between the face of the first electrode and the face of the second electrode, and an access hole through the second electrode that is capable of allowing a fluid to enter and leave the cavity.

11. The device of claim 10 wherein the face of the first electrode is separated from the face of the second electrode by a distance that is between 10 and 200 nm.

12. The device of claim 10 wherein the conducting diamond is nanocrystalline diamond.

13. The device of claim 10 wherein the conducting diamond is boron doped diamond.

14. The device of claim 10 wherein both the first a second electrodes are comprised of conducting diamond.

15. The device of claim 10 wherein the first electrode is comprised of conducting diamond and the height of the first electrode is between 300 nm and 1000 nm.

16. The device of claim 10 wherein the first or the second electrode is comprise of gold or platinum.

17. A system comprising, a computer operably coupled to an integrated circuit chip wherein the integrated circuit chip comprises an array of transducers disposed on a surface of the integrated circuit chip, a fluidic system capable of supplying fluids to the surface of the integrated circuit chip comprising the array of transducers, wherein transducers that make up the array are electrically coupled to and individually addressable through electronics in the integrated circuit chip, and wherein a transducer comprises:
a first electrode and a second electrode, wherein the first or the second electrode is comprised of conducting diamond, wherein the first and second electrodes are independently coupled to the integrated circuit chip through which voltage can be applied to the first and second electrodes and a current measured from each of the first and second electrodes independently, and wherein the first electrode has a face and the second electrode has a face and the face of the first electrode is separated from the face of the second electrode by a distance that is less than 500 nm, a cavity capable of containing a fluid between the face of the first electrode and the face of the second electrode, and an access hole through the second electrode that is capable of allowing a fluid to enter and leave the cavity.

18. The device of claim 17 the face of the first electrode is separated from the face of the second electrode by a distance that is between 10 and 200 nm.

19. The device of claim 17 wherein the array comprises at least 1000 transducers and at least 90% of the transducers are functional transducers.

20. The device of claim 17 wherein the conducting diamond is nanocrystalline diamond.

21. The device of claim 17 wherein the conducting diamond is boron doped diamond.

22. The device of claim 17 wherein both the first and second electrodes are comprised of conducting diamond.

23. The device of claim 17 wherein the first or the second electrode is comprise of gold or platinum.

24. The device of claim 17 wherein the computer is configured to perform data analysis using current measurements from one of the first or the second electrode wherein the one of the first or second electrode from which the current is measured is comprised of conducting diamond.

* * * * *